United States Patent
Chow et al.

(10) Patent No.: US 7,670,579 B2
(45) Date of Patent: *Mar. 2, 2010

(54) NANOSTRUCTURED BIOACTIVE MATERIALS PREPARED BY DUAL NOZZLE SPRAY DRYING TECHNIQUES

(75) Inventors: Laurence C. Chow, Potomac, MD (US); Limin Sun, Germantown, MD (US)

(73) Assignee: American Dental Association Foundation, Chicago, IL (US)

( * ) Notice: Subject to any disclaimer, the term of this patent is extended or adjusted under 35 U.S.C. 154(b) by 1189 days.

This patent is subject to a terminal disclaimer.

(21) Appl. No.: 11/228,139

(22) Filed: Sep. 16, 2005

(65) Prior Publication Data

US 2006/0110306 A1    May 25, 2006

Related U.S. Application Data

(63) Continuation-in-part of application No. 11/100,218, filed on Apr. 6, 2005, now Pat. No. 7,390,335.

(60) Provisional application No. 60/559,884, filed on Apr. 6, 2004.

(51) Int. Cl.
C04B 35/447 (2006.01)
C01B 25/26 (2006.01)
C01B 25/32 (2006.01)
C01F 11/22 (2006.01)
C01B 33/24 (2006.01)

(52) U.S. Cl. ............... 423/305; 23/293 A; 423/308; 423/331; 423/490; 423/659

(58) Field of Classification Search ............... 23/293 A; 977/776; 423/305, 308, 331, 490, 659
See application file for complete search history.

(56) References Cited

U.S. PATENT DOCUMENTS

| | | | |
|---|---|---|---|
| 3,366,444 A * | 1/1968 | Laferty, Jr. et al. | 423/490 |
| 4,897,250 A | 1/1990 | Sumita | |
| 5,034,352 A | 7/1991 | Vit et al. | |
| 5,585,318 A | 12/1996 | Johnson et al. | |
| 6,013,591 A | 1/2000 | Ying et al. | |
| 6,033,780 A | 3/2000 | Nishioka et al. | |
| 6,558,512 B2 | 5/2003 | Ueno et al. | |
| 6,592,989 B1 | 7/2003 | Senna et al. | |
| 7,150,862 B2 * | 12/2006 | Ishikawa et al. | 423/308 |
| 7,390,335 B2 * | 6/2008 | Chow | 23/293 A |

OTHER PUBLICATIONS

International Search Report, International Application No. PCT/US05/33406; date of mailing Apr. 11, 2006, 2 pages.

(Continued)

*Primary Examiner*—Wayne Langel
(74) *Attorney, Agent, or Firm*—Banner & Witcoff, Ltd.

(57) ABSTRACT

Nano-particles of calcium and phosphorous compounds are made in a highly pure generally amorphous state by spray drying a weak acid solution of said compound and evaporating the liquid from the atomized spray in a heated column followed by collection of the precipitated particles. Hydroxyapatite (HA) particles formed by such apparatus and methods are examples of particle manufacture useful in bone and dental therapies. Dual nozzle spraying techniques are utilized for generally insoluble compounds.

11 Claims, 5 Drawing Sheets

OTHER PUBLICATIONS

J. Arends and J. Christoffersen; Nature and Role of Loosely Bound Fluoride in Dental Caries; Presented at a Joint IADR/ORCA International Symposium on Flourides: Mechanisms of Action and Recommendations for Use, held Mar. 21-24, 1989, Callaway Gardens Conference Center, Pine Mountain, Georgia.

O. Bermudez, M.G. Boltong, F.C.M. Driessens. J.A. Planell; Development of an octocalcium phosphate cement; Journal of Materials Science: Materials in Medicine 5 (1994) 144-146.

Enrico Bertoni, Adriana Bigi, Giuseppe Falini, Silvia Panzavolta and Norberto Roveri; Hydroxyapatite/polyacrylic acid nanocrystals; J. Mater. Chem., 1999, 9, 779-782.

Enrico Bertoni, Adriana Bigi, Gianna Cojazzi, Massimo Gandolfi, Silvia Panzavolta, Norberto Roveri; Nanocrystals of magnesium and fluoride substituted hydroxyapatite; Journal of Inorganic Biochemistry; 72 (1998) 29-35.

Proceedings of the Biomedical and Biological Applications of Ceramics and Glass Symposium, presented at the 98th Annual Meeting of the American Ceramic Society, held in Indianapolis, IN, Apr. 25-27, 1994, and the Workshop of Ceramics for Biomedical Applications, held in Alfred, NY, Jun. 8-10, 1994.

Susmita Bose and Susanta Kumar Saha; Synthesis and Characterization of Hydroxyapatite Nanopowders by Emulsion Technique; Chem. Mater. 2003, 15, 4464-4469.

W.E. Brown and L.C. Chow; A New Calcium Phosphate, Water-Setting Cement; Cements Research Progress 1986, P.W. Brown, Ed., Westerville, Ohio; American Ceramic Society, pp. 352-379; American Dental Association Health Foundation, Gaithersburg, MD.

C.S. Chai, B. Ben-Nissan; Bioactive nanocrystalline sol-gel hydroxyapatite coatings; Journal of Materials Science: Materials in Medicine 10 (1999) 465-469.

James Y. M. Chau, DDS, MS, Jeffrey W. Hutter, DMD, MEd, Thomas O. Mork, DDS, and Brian K. Nicoll, DDS; An In Vitro Study of Furcation Perforation Repair Using Calcium Phosphate Cement; Journal of Endodontics, vol. 23, No. 9, Sep. 1997.

Fei Chen, Zhou-Cheng Wang, Chang-Jian Lin; Preparation and characterization of non-sized hydroxyapatite particles and hydroxyapatite/chitosan nano-composite for use in biomedical materials; Materials Letters 57 (2002) 858-881.

A. Maria Cherng, DDS, MS, Laurence C. Chow, PhD, and Shozo Takagi, PhD; In Vitro Evaluation of a Calcium Phosphate Cement Root Canal Filler/Sealer Journal of Endodontics, vol. 27, No. 10, Oct. 2001.

A.M. Cherng, L.C. Chow, S. Takagi; Reduction in dentin permeability using mildly supersaturated calcium phosphate solutions; Archives of Oral Biology, (2004) 49, 91-98.

L.C. Chow, S. Hirayama, S. Takagi, E. Parry; Diametral Tensile Strength and Compressive Strength of a Calcium Phosphate Cement: Effect of Applied Pressure; American Dental Association Health Foundation, Paffenbarger Research Center, Polymers Division, National Institute of Standards and Technology, Gaithersburg, MD; Received Feb. 14, 2000, accepted Apr. 26, 2000.

A. Cuneyt Tas; Synthesis of biomimetic Ca-hydroxyapatite powders at 37 C in synthetic body fluids; Biomaterials 21 (2000) 1429-1438; Elsevier Science Ltd.

Frank C. den Boer, Burkhard W. Wippermann, Taco J. Bokhuis, Peter Patka, Fred C. Bakker, Henk J. Th.M. Haarman; Healing of segmental bone defects with granular porous hydroxyapatite augmented with recombinant human osteogenic protein-1 or autologous bone marrow; Journal of Orthopaedic Research 21 (2003) 521-528; Elsevier Science Ltd.

Xianmo Deng, Jianyuan Hao, Changsheng Wang; Preparation and mechanical properties of nanocomposites of poly(D,L-lactide) with Ca-deficient hydroxyapatite nanocrystals; Biomaterials 22 (2001) 2867-2873; Elsevier Science Ltd.

Sabine H. Dickens, Glenn M. Flaim, Shozo Takagi; Mechanical properties and biochemical activity of remineralizing resin-based Ca-PO4 cements; Dental Materials 19 (2003) 558-566; Elsevier Science Ltd. on behalf of Academy of Dental Materials.

M.P. Ginebra, E. Fernandez, E.A.P. De Maeyer. R.M.H. Verbeeck, M.G. Boltong, J. Ginebra, F.C.M. Driessens, and J.A. Planell; Setting Reaction and Hardening of an Apatitic Calcium Phosphate Cement; J Dent Res 76(4), 905-912, Apr. 1997.

Mei Huang, Jianqing Feng, Jianxin Wang, Xingdong Zhang, Yubao Li, Yonggang Yan; Synthesis and characterization of nano-HA/PA66 composites; Journal of Materials Science: Materials in Medicine 14 (2003) 655-660; Kluwer Academic Publishers.

Willim L. Jaffe, M.D. and David F. Scott, M.D.; Total Hip Arthroplasty with Hydroxyapatite-Coated Prostheses; The Journal of Bone and Joint Surgery, Incorporated, vol. 78-A, No. 12, Dec. 1996.

Masanori Kikuchi, Soichiro Itoh, Hizuko Ichinose, Kenichi Shinomiya, Junzo Tanaka; Self-organization mechanism in a bone-like hydroxyapatite/collagen nanocomposite synthesized in vitro and its biological reaction in vivo; Biomaterials 22 (2001) 1705-1711; Elsevier Science Ltd.

S.W.K. Kweh, K.A. Khor, P. Cheang; The production and characterization of hydroxyapatite (HA) powders; Journal of Materials Processing Technology 89-90 (1999) 373-377; Elsevier Science S.A.

Pierre Layrolle, Atsuo Ito, and Tetsuya Tateishi; Sol-Gel Synthesis of Amorphous Calcium Phosphate and Sintering into Microporous Hydroxyapatite Bioceramics; Journal of the American Ceramic Society 81(6) 1421-28 (1998).

D. Duke Lee, PhD, Ali Tofighi, PhD, Maria Aiolova, MS, Pramod Chakravarthy, MS; Anthony Catalano, MS, Anthony Majahad, BS, and David Knaack, PhD; a-BSM: A Biomimetic Bone Substitute and Drug Delivery Vehicle; Clinical Orthopaedics and Related Research, No. 367S, pp. S396-S405, 1999, Lippincott Williams & Wilkins, Inc.

Racquel Z. Legeros; Calcium Phophate Biomaterials in Preventive and Restorative Dentistry; Calcium Phosphates in Oral Biology and Medicine; 15 Monographs in Oral Science.

Li Yubao, X. De Groot, J. De Wijn, C.P.A.T. Klein, S.V.D. Meer; Morphology and composition of nanograde calcium phosphate needle-like crystals formed by simple hydrothermal treatment; Materials Science: Materials in Medicine 5 (1994) 326-331; Chapman & Hall.

G.K. Lim, J. Wang, S.C. Ng, and L.M. Gan; Formation of Nanocrystalline Hydroxyapatite in Nonionic Surfactant Emulsions; Langmuir 1999, 15, 7472-7477; American Chemical Society.

G.K. Kim, J. Wang, S.C. Ng, and L.M. Gan; Nanosized hydroxyapatite powders from microemulsions and emulsions stabilized by a biodegradable surfactant; Journal of Materials Chemistry, 1999, 9, 1635-1639.

P. Luo and T.G. Nieh; Preparing hydroxyapatite powders with controlled morphology; Biomaterials 1996, vol. 17 No. 20; Elsevier Science Limited.

P. Luo, T.G. Nieh; Synthesis of ultrafine hydroxyapatite particles by a spray dry method; Materials Science and Engineering: C3 (1995) 75-78; Elsevier Science S.A.

Michael A. McBride, Russell O. Gilpatrick, Wiley L. Fowler; The effectiveness of sodium fluoride iontophoresis in patients with sensitive teeth; Quintessence International, vol. 22, No. 8/1991, 637-640.

E. Mejdoubi, J.L. Lacout, J.C. Heughebaert and P. Michaud; Optimization of a Hydraulic Calcium Phosphate Cement; Advanced Materials Research vols. 1-2 (1994) pp. 163-172; Scitec Publications, Switzerland.

Akira Ogose, Tetsuo Hotta, Hiroshi Hatano, Hiroyuki Kawashima, Kunihiko Tokunaga, Naoto Endo, Hajime Umezu; Hislological Examination of B-Tricalcium Phosphate Graft in Human Femur; Wiley Periodicals, Inc. 2002.

M.J. Phillips, J.A. Darr, Z.B. Luklinska, I. Rehman; Synthesis and characterization of nano-biomaterials with potential osteological applications; Kluwer Academic Publishers, 2003.

Phillips RW (1973); Physical Properties of Dental Materials, Biological Considerations; Skinners Science of Dental Materials, Philadelphia, PA, WB Saunders Company, pp. 28-54.

Imin Qi; Jiming Ma, Humin Cheng, Zhenguo Zhao; Microemulsion-mediated synthesis of calcium hydroxyapatite fine powders.

Sang-Hoon Rhee, Uasushi Suetsuga, Junzo Tanaka; Biomimetic configurational arrays of hydroxyapatite nanocrystals on bio-organics; Biomaterials 22 (2001) 2843-2847; Elsevier Science Ltd.

R. Rodriguez, J. Coreno, J.A. Arenas. V.M. Castano; Nanocomposites Produced by Growth of Hydroxyapatite onto Silica Particles Prepared by the Sol-Gel Method; Advanced Composites Letters, vol. 5, No. 1 1996.

S. Sarig, F. Kahana; Rapid formation of nanocrystalline apatite; Journal of Crystal Growth 237-239 (2002) 55-59; Elsevier Science B.V.

Richard S. Schwartz, DDS, Michael Mauger, DMD, David J. Clement, DDS, William A. Walker, III, DDS, MS; Mineral Trioxide Aggregate: A New Material for Endodontics; JADA, vol. 130, Jul. 1999.

M. Shirkhanzadeh; Direct formation of nanophase hydroxyapatite on cathodically polarized electrodes; Material Science, Materials in Medicine.

C.C. Silva, A.G. Pinheiro, M.A.R. Miranda, J.C. Goes, A.S.B. Sombra; Structural properties of hydroxyapatite obtained by mechanosynthesis; Solid State Sciences 5 92003) 553-558; Elsevier S.A.S.

D. Skrtic, J.M. Antonucci, E.D. Eanes, N. Eidelman Dental Composites based on hybrid and surface-modified amorphous calcium phosphates; Biomaterials 25 (2004) 1141-1150; Elsevier Ltd.

Akiyoshi Sugawara,. DDS, PhD, Laurence C. Chow, PhD, Shozo Takagi, PhD, and Hanan Chohayeb DDS; In Vitro Evaluation of the Sealing Ability of a Calcium Phosphate Cement When Used as a Root Canal Sealer-Filler; Journal of Endodontics, vol. 16, No. 4, Apr. 1990.

S. Takagi, L.C. Chow, B.A. Sieck; Deposition of Loosely Bound and Firmly Bound Fluorides on Tooth Enamel by an Acidic Gel Containing Fluorosilicate and Monocalcium Phosphate Monohydrate; Caries Research 1992, 26, 321-327; S. Karger AG, Basel, Switzerland.

J. Tourent-Burgues, J. Gomez-Morales, A. Lopez Macipe, R. Rodriguez-Clemente; Continuous Precipitation of Hydroxyapatile from Ca/Citrate/Phosphate Solutions using Microwave Heating; Cryst. Res. Technol. 34, 1999, 5-6, 757-762.

G. L. Vogel, Y. Mao, C.M. Carey, L.C. Chow and S. Takagi; In vivo Fluoride Concentrations Measured for Two Hours After a NaF or a Novel Two-solution Rinse; Journal of Dental Research, Mar. 1992.

G. L. Vogel, Z. Zhang, C.M. Carey, A. Ly, L.C. Chow, and H.M. Proskin; Composition of Plaque and Saliva Following a Sucrose Challenge and Use of an a-tricalcium-phosphate-containing Chewing Gum; Journal of Dental Research, vol. 77, No. 3, 1998.

G. L. Vogel, Z. Zhang, C.M. Carey, A. Ly, L.C. Chow. and H.M. Proskin; Composition of Plaque and Saliva Following use of an a-Tricalcium-phosphate-containing Chewing Gum and a Subsequent Sucrose Challenge; Journal of Dental Research, vol. 79, No. 1, 2000.

Wei Jie, Li Yubao, Chen Weiqun, Auo Yi; A study on nano-composite of hydroxyapatite and polyamide; Kluwer Academic Publishers, 2003.

I. Yamaguchi, K. Tokuchi, H. Fukuzaki, Y. Koyama, K. Takakuda, H. Monma and J. Tanaka; Preparation and Mechanical Properties of Chitosan/Hydroxyapatite Nanocomposites; Key Engineering Materials vols. 192-195 (2001) pp. 673-676; Proceedings of the 13$^{th}$ Int. Symp. on Ceramics in Medicine, Bologna, Italy, Nov. 22-26, 2000 pp. 673-676; Trans Tech Publications, Switzerland 2001.

K.C.B. Yeong, J. Wang, S.C. Ng; Mechanochemical synthesis of nanocrystalline hydroxyapatite from CaO and CaHPO4; Biomaterials 22 (2001) 2705-2712; Elsevier Science Ltd. 2001.

S. Zhang, K.E. Gonsalves; Preparation and characterization of thermally stable nanohydroxyapatite; Journal of Materials Science: Materials in Medicine (1997) 25-28; Chapman & Hall 1997.

Enrico Bertoni, Adriana Bigi, Giuseppe Falini, Silvia Panzavoilta and Norberto Roveri; Hydroxyapatite/polyacrylic acid nanocrystals; Department of Chemistry, 'G. Ciamician', University of Bologna, Italy; Dec. 18, 1998.

A.M. Chrng, L.C. Chow, S. Takagi; Reduction in Dentin Permeability Using Mildly Supersaturated Calcium Phosphate Solutions; American Dental Association Health Foundation, Paffenbarger Research Center, National Institute of Standards and Technology, Gaithersburg, MD 20899, Jul. 14, 2003.

Akira Ogose, Tetsuo Hotta, Hiroshi Hatano, Hiroyuki Kawashima, Kunihiko Tokunaga, Naoto Endo, Hajime Umezu; Histological Examination of B-Tricalcium Phosphate Graft in Human Femur; Mar. 23, 2002, Wiley Periodicals, Inc.

Racquel Z. Legeros; Calcium Phosphates in Enamel, Dentin and Bone; Mongraphs in Oral Science.

J. Arends and J. Christoffersen, Nature and Role of Loosely Bound Fluoride in Dentaal Caries; Presented at a joint IADR/ORCA International Sympsium on Fluorides; Mechanisms of Action and Recommendations for Use, held Mar. 21-24, 1989, Callaway Gardens Conference Center, Pine Mountain, Georgia.

O. Bermudez, M.G. Boltong, F.C.M. Driessens, J.A. Planell; Development of an Octocalcium Phosphate Cement, Journal of Materials Science Materials in Medicine 5 (1994) 144-146.

Enrico Bertoni, Adriana Bigi, Giuseppe Falini, Silvia Panzavolta and Norberto Roveri; Hydroxyapatite/Polyacrylic Acid Nanocrystals; J. Mater. Chem., 1999, 9, 779-782.

Enrico Bertoni, Adriana Bigi, Gianna Cojazzi, Massimo Gandolfi, Silvia Panzavolta, Norberto Roveri; Nanocrystals of Magnesium and Fluoride Substituted Hydroxyapatite; Journal of inorganic Biochemistry; 72 (1998) 29-35.

Proceedings of the Biomedical and Biological Applications of Ceramics and Glass Symposium, presented at the 96th Annual Meeting of the American Ceramic Society, held in Indianapolis, IN, Apr. 25-27, 1994, and the Workshop on Ceramics for Biomedical Applications, held in Alfred, NY, Jun. 8-10, 1994.

W.E. Brown and L.C. Chow; A New Calcium Phosphate, Water-Setting Cement, Cements Research Progress 1986, P.W. Brown, Ed., Westerville, Ohio; American Ceramic Society, pp. 352-379; American Dental Association Health Foundation, Gaithersburg, MD.

C.S. Chai, B. Ben-Nissan, Bioactive Nanocrystalline Sol-gel Hydroxyapatite Coatings; Journal of Materials Science: Materials in Medicine 10 (1999) 465-469.

James Y.M. Chau, DDS, MS, Jeffrey W. Hutter, DMD, MEd. Thomas O. Mork, DDS, and Brian K. Nicoll, DDS; An in Vitro Study of Furcation Perforation Repair Using Calcium Phosphate Cement; Journal of Endodontics, vol. 23, No. 9, Sep. 1997.

Fei Chen, Zhou-Cheng Wang, Chang-Jian Lin; Preparation and Characterization of Nano-Sized Hydroxyapatite Particles and Hydroxyapatite/Chitosan Nano-Composite For Use in Biomedical Materials; Materials Letters 57 (2002) 858-861.

A. Maria Cherng, DDS, MS, Laurence C. Chow, PhD, and Shozo Takagi, PhD; In Vitro Evaluation of a Calcium Phosphate Cement Root Canal Filler/Sealer, Journal of Endodontics, vol. 27, No. 10, Oct. 2001.

A.M. Cherng, L.C. Chow, S. Takagi; Reduction in Dentin Permeability Using Mildly Supersaturated Calcium Phosphate Solutions; Archives of Oral Biology, (2004) 49, 91-98.

L.C. Chow, S. Hirayama, S. Takagi, E. Parry; Diametral Tensile Strength and Compressive Strength of a Calcium Phosphate Cement: Effect of Applied Pressure; American Dental Association Health Foundation, Paffenbarger Reseach Center, Polymers Division, National Institute of Standards and Technology, Gaithersburg, MD; Apr. 26, 2000.

A. Cuneyt Tas; Synthesis of Biometic Ca-hydroxyapatite Powders at 37 C in Synthetic Body Fluids; Biomaterials 21 (2000) 1429-1438; Elsevier Science Ltd.

Frank C. den Boer, Burkhard W. Wippermann, Taco J. Blokhuis, Peter Patka, Fred C. Bakker, Henk J. Th.M. Haarman; Healing of Segmental Bone Defects With Granular Porous Hydroxyapatite Augmented With Recombinant Human Osteogenic Protein-1 or Autologous Bone Marrow; Journal of Orthopaedic Research 21 (2003) 521-528; Elsevier Science Ltd.

Xianmo Deng, Jianyuan Hao, Changsheng Wang; Preparation and Mechanical Properties of Nanocomposites of Poly(D.L-lactide) With Ca-deficient Hyrdroxyapatite Nanocrystals; Biomaterials 22 (2001) 2867-2873, Elsevier Science Ltd.

Sabine H. Dickens, Glenn M. Flaim, Shozo Takagi; Mechanical Properties and Biochemical Activity of Remineralizing Resin-Based Ca-PO4 Cements, Dental Materials 19 (2003) 558-566, Elsevier Science Ltd. on Behalf of Academy of Dental Materials.

M.P. Ginebra, E. Fernandez, E.A.P. De Maeyer, R.M.H. Verbeeck, M.G. Boltong, J. Ginebra, F.C.M. Driessens, and J.A. Planell; Setting Reaction and Hardening of an Apatitic Calcium Phosphate Cement; J. Dent Res 76 (4), 905-912, Apr. 1997.

Mei Huang, Jianqing Feng, Jianxin Wang, Xingdong Zhang, Yubao Li, Yonggang Yan; Synthesis and Characterization of Nano-HA/

PA66 Composites; Journal of Materials Science; Materials in Medicine 14 (2003) 650-660; Kluwer Academic Publishers.

William L. Jaffe, M.D. and David F. Scott, M.D.; Total Hip Arthroplasty With Hydroxyapatite-Coated Prostheses; The Journal of Bone and Joint Surgery, Incorporated, vol. 78-A, No. 12, Dec. 1996.

Masanori Kikuchi, Soichiro Itoh, Shizuko Ichinose, Kenichi, Shinomiya, Junzo Tanaka; Self-organization Mechanism in a Bone-Like Hydroxyapatite/Collagen Nanocomposite Synthesized in Vitro and its Biological Reaction in Vivo; Biomaterials 22 (2001) 1705-1711; Elsevier Science Ltd.

S.W.K. Kweh, K.A. Khor, P. Cheang; The Production and Characterization of Hydroxyapatite (HA) Powders; Journal of Materials Processing Technology 89-90 (1999) 373-377; Elsevier Science S.A.

Pierre Layrolle, Atsuo Ito, and Tetsuya Tateishi; Sol-Gel Synthesis of Amorphous Calcium Phosphate and Sintering into Microporous Hydroxyapatite Bioceramics; Journal of the American Ceramic Society 81 (6) 1421-28 (1998).

D. Duke Lee, PhD, Ali Tofighi, PhD, Maria Aiolova, MS, Pramod Chakravarthy, MS, Anthony Catalano, MS, Anthony Majahad, BS, and David Knaack, PhD; a-BSM: A Biomimetic Bone Substitute and Drug Delivery Vehicle; Clinical Orthopaedics and Related Research, No. 367S, pp. S396-S405, 19999, Lippincott Williams & Wilkins, Inc.

Racquel Z. Legeros, Calcium Phosphate Biomaterials in Preventive and Restorative Dentistry; Calcium Phosphates in Oral Biology and Medicine; 15 Monographs in Oral Science pp. 154-171.

Li Yubao, K. De Groot; J. De Wijn, C.P.A.T. Klein, S.V.D. Meer, Morphology and Composition of Nanograde Calcium Phosphate Needle-Like Crystals Formed by Simple Hydrothermal Treatment; Materials Science: Materials in Medicine 5 (1994) 326-331; Chapman & Hall.

G.K. Lim, J. Wang, S.C. Ng, and L.M. Gan; Nanosized Hydoxyapatite Powders From Microemulsions and Emulsions Stabilized by a Biodegradable Surfactant; Journal of Materials Chemistry, 1999, 9, 1635-1639.

P. Luo and T.G. Nieh; Preparing Hydroxyapatite Powders With Controlled Morphology, Biomaterials 1996, vol. 17 No. 20; Elsevier Science Limited.

P. Luo and T.G. Nieh; Synthesis of Ultrafine Hydroxyapatite Particles by a Spray Dry Method, Materials Science and Engineering: C 3 (1995) 75-78; Elsevier Science S.A.

Michael A. McBride, Russell O. Gilpatrick, Wiley L. Fowler; The Effectiveness of Sodium Fluoride Iontophoresis in Patients With Sensitive Teeth; Quintessence International, vol. 22, No. 8/1991, 637-640.

E. Mejdoubi, J.L. Lacout J.C. Heughebaert and P. Michaud; Optimization of a Hydraulic Calcium Phosphate Cement, Advanced Materials Research vols. 1-2 (1994) pp. 163-172; Scitec Publications, Switzerland.

Akira Ogose, Tetsuo Hotta, Hiroshi Hatano, Hiroyuki Kawashima, Kunihiko Tokunaga, Naoto Endo, Hajime Umezu, Histological Examination of B-Tricalcium Phosphate Graft in Human Femur, Wiley Periodicals, Inc. 2002.

M.J. Phillips, J.A. Darr, Z.B. Luklinska, I. Rehman, Synthesis and Characterization of Nano-Biomaterials With Potential Osteological Applications; Kluwer Academic Publishers, 2003 pp. 875-882.

Imin Qi; Jiming Ma, Humin Cheng, Zhenguo Zhao; Microemulsion-Mediated Synthesis of Calcium Hydroxyapatite Fine Powders.

Sang-Hoon Rhee, Yasushi Suetsuga, Junzo Tanaka, Biomimetic Configurational Arrays of Hydroxyapatite Nanocrystals on Bio-Organics, Biomaterials 22 (2001) 2843-2847; Elsevier Science Ltd.

R. Rodriguez, J. Coreno, J.A. Arenas, V.M. Castano; Nanocomposites Produced by Growth of Hydroxyapatite onto Silica Particles Prepared by the Sol-Gel Method; Advanced Composites Letters, vol. 5, No. 1 1996.

S. Sarig, F. Kahana; Rapid Formation of Nanocrystalline Apatite; Journal of Crystal Growth 237-239 (2002) 55-59; Elsevier Science B.V.

Richard S. Schwartz, DDS, Michael Mauger, DMD, David J. Clement, DDS, William A. Walker, III, DDS, MS; Mineral Trioxide Aggregate: A New Material for Endodontics; JADA, vol. 130, Jul. 1999, pp. 967-975.

M. Shirkhanzadeh; Direct Formation of Nanophase Hydroxyapatite on Cathodically Polarized Electrodes; Journal of Material Science Materials in Medicine pp. 67-72.

C.C. Silva, A.G. Pinheiro, M.A.R. Miranda, J.G. Goes, A.S.B. Sombra; Structural Properties of Hydroxyapatite Obtained by Mechanosynthesis; Solid State Sciences 5 (2003) 553-558; Elsevier S.A.S.

D. Skrtic, J.M. Antonucci, E.D. Eanes, N. Eidelman, Dental Composites Based on Hybrid and Surface-Modified Amorphous Calcium Phosphates; Biomaterials 25 (2004) 1141-1150; Elsevier Ltd.

Akiyoshi Sugawara, DDS, PhD, Laurence C. Chow, PhD, Shozo Takagi, PhD, and Hanan Chohayeb, DDS; In Vitro Evaluation of the Sealing Ability of a Calcium Phosphate Cement When Used as a Root Canal Sealer-Filler; Journal of Endodontics, vol. 16, No. 4, Apr. 1990.

J. Torrent-Burgues, J. Gomez-Morales, A. Lopez-Macipe, R. Rodriguez-Clemente; Continuous Precipitation of Hydroxyapatite From Ca/Citrate/Phosphate Solutions Using Microwave Heating, Cryst. Res. Technol. 34, 1999, 5-6, 757-762.

G.L. Vogel, Y. Mao, C.M. Carey, L.C. Chow and S.Takagi; In Vivo Fluoride Concentrations Measured for Two Hours After a NaF or a Novel Two-Solution Rinse; Journal of Dental Research, Mar. 1992.

G.L. Vogel, Z. Zhang, C.M. Carey, A. Ly, L.C. Chow, and H.M. Proskin; Composition of Plaque and Saliva Following a Sucrose Challenge and Use of an a-TriCalcium-Phosphate-Containing Chewing Gum; Journal of Dental Research, vol. 77, No. 3, 1998.

G.L. Vogel, Z. Zhang, C.M. Carey, A. Ly, L.C. Chow, and H.M. Proskin,; Composition of Plaque and Saliva Following Use of an a-TriCalcium-Phosphate-Containing Chewing Gum and a Subsequent Sucrose Challenge ; Journal of Dental Research, vol. 79, No. 1, 2000.

Wei Jie, Li Yubao, Chen Weiqun, Zuo Yi; A Study on Nano-Composite of Hydroxyapatite and Polyamide, Kluwer Academic Publishers, 2003.

I. Yamaguchi, K. Tokuchi, H. Fukuzaki, Y. Koyama, K. Takakuda, H. Monma and J. Tanaka, Preparation and Mechanical Properties of Chitosan/Hydroxyapatite Nancomposites, Key Engineering Materials vols. 192-195 (2001) pp. 673-676.

K.C.B. Yeong, J. Wang, S.C. Ng, Mechanochemical Synthesis of Nanocrystalline Hydroxyapatite from CaO and CaHPO4, Biomaterials 22 (2001) 2705-2712 Elsevier Science Ltd.

S. Zhang, K.E. Gonsalves, Preparation and Characterization of Thermally Stable Nanohydroxyapatite, Journal of Materials Science Materials in Medicine (1997) 25-28, Chapman & Hall 1997.

Racquel Z. Legeros, Calcium Phosphates in Enamel, Dentin and Bone, Calcium Phosphates in Oral Biology and Medicine, Mongraphs on Oral Science, Editor Howard M. Myers, pp. 108-129.

Laurence C. Chow, Limin Sun and Bernard Hockey, Properties of Nanostructured Hydroxyapatite Prepared by a Spray Drying Technique, Journal of Research of the National Institute of Standards and Technology, vol. 109, No. 6, (2004) pp. 543-551.

Fei Chen, Zhou-Cheng Wang, Chang-Jian Lin; Preparation and Characterization of Nano-Sized Hydroxyapatite Particles and Hydroxyapatite/Chitosan Nano-Composite For Use in Biomedical Materials; Materials Letters 57 (2002) 858-861.

M.P. Ginebra, E. Fernandez, E.A.P De Maeyer, R.M.H. Verbeeck, M.G. Boltong, J. Ginebra, F.C.M. Driessens, and J.A. Planell; Setting Reaction and Hardening of an Apatitic Calcium Phosphate Cement; J. Dent Res 76 (4), 905-912, Apr. 1997.

D. Duke Lee, PhD, Ali Tofighi, PhD, Maria Aiolova, MS, Pramod Chakravarthy, MS, Anthony Catalano, MS, Anthony Majahad, BS, and David Knaack, PhD; a-BSM: A Biomimetic Bone Substitute and Drug Delivery Vehicle; Clinical Orthopaedics and Related Research, No. 367S, pp. S396-S405, 19999, Lippincott Williams & Wilkins, Inc.

G.L. Vogel, Z. Zhang, C.M. Carey, A. Ly. L.C. Chow, and H.M. Proskin; Composition of Plaque and Saliva Following a Sucrose Challenge and Use of an a-TriCalcium-Phosphate-Containing Chewing Gum; Journal of Dental Research, vol. 77, No. 3, 1998.

* cited by examiner

SEM of a nano CaF₂ sample

TEM of a nano size calcium fluoride material showing conglomerates consisting of particles about 10 to 15 nm in sizes.

NANOSTRUCTURED BIOACTIVE MATERIALS PREPARED BY DUAL NOZZLE SPRAY DRYING TECHNIQUES

CROSS REFERENCE OF RELATED APPLICATIONS

This is a continuation-in-part utility application derived from and incorporating by reference a previously filed provisional application entitled Nanostructured Bioactive Material Prepared by Spray Drying Techniques filed Apr. 6, 2004 as Ser. No. 60/559,884 and a subsequent utility application entitled Nanostructured Bioactive Materials Prepared by Spray Drying Techniques, filed Apr. 6, 2005 as Ser. No. 11/100,218 incorprated herewith by reference and for which priority is claimed.

REFERENCE TO RESEARCH GRANTS AND GOVERNMENT LICENSE

This invention was made during research activities that were supported in part by Grants DE11789 from the NIDCR to the ADAF and carried out at the National Institute of Standards and Technology.

BACKGROUND OF THE INVENTION

In a principal aspect the present invention comprises apparatus and preparation methods, by a spray drying technique for forming nanostructured particles of bioactive materials that have high reactivity, small particle sizes and high surface areas. Such manufactured materials have performance advantages in a range of biomedical applications.

The mineral component of bone and teeth consists primarily of non-stoichiometric and highly substituted hydroxyapatite (HA) in poorly crystalline or nearly amorphous forms. The "impurity" components that are present at significant levels in such biominerals include sodium, potassium, magnesium, and strontium substituting for calcium, carbonate for phosphate, and chloride and fluoride for hydroxyl ions. Because HA is stable under in vivo conditions and is osteoconductive, synthetic HA has been widely used in hard tissue repair application, such as implant coatings and bone substitutes. Other calcium phosphate phases have also been shown to be highly biocompatible and/or osteoconductive. As a result, with the exception of fluorapatite (FA), the calcium phosphate compounds listed in Table 1 have been used in some form of bone repair applications.

TABLE 1

Calcium Phosphate Compounds that Have Being Used in Bone Repair Applications

| Compound | Formula | Bone repair applications |
|---|---|---|
| Monocalcium phosphate monohydrate (MCPM) | $Ca(H_2PO_4)2H_2O$ | Components of calcium phosphate cement (CPC) [Mejdoubi et al., 1994] |
| Dicalcium phosphate anhydrous (DCPA) | $CaHPO_4$ | CPC component [Brown and Chow, 1987] |
| Dicalcium phosphate dehydrate (DCPD) | $CaHOP_42H_2O$ | CPC product [Bohner et al., 1995]; CPC component [Brown and Chow, 1987] |
| Octacalcium phosphate (OCP) | $Ca_8H_2(PO_4)_65H_2O$ | CPC product [Bermudez et al., 1994] |
| α-Tricalcium phosphate (α-TCP) | $\alpha\text{-}Ca_3(PO_4)_2$ | CPC component [Ginebra et al. 1997] |
| β-Tricalcium phosphate (β-TCP) | $\beta\text{-}Ca_3(PO_4)_2$ | CPC component [Mejdoubi et al., 1994]; Granular bone graft [Ogose et al., 2002] |
| Amorphous calcium phosphate (ACP) | $Ca_3(PO_4)_2$ | CPC component [Lee et al., 1999] |
| Hydroxyapatite (HA) | $Ca_5(PO_4)_3OH$ | CPC product [Brown and Chow, 1987]; granular bone graft [den Boer et al., 2003]; Implant coating [Jaffe and Scott, 1996] |
| Fluorapatite (FA) | $Ca_5(PO_4)_3F$ | |
| Tetracalcium phosphate (TTCP) | $Ca_4(PO_4)_2O$ | CPC component [Brown and Chow, 1987] |

Calcium phosphate compounds are also useful in various dental applications. For example, a slurry or gel that contained MCPM and fluoride was used as topical F agents that produced significant amounts of both tooth-bound and loosely bound F deposition on enamel surfaces. A chewing gum that contained α-TCP as an additive released sufficient amounts of calcium and phosphate ions into the oral cavity and significantly alleviated cariogenic challenges produced by sucrose. A calcium phosphate cement that contained TTCP and DCPA was shown to provide effective apical seal when used as a root canal filler/seal, or as a sealer with as a retrievable master cone. The cement was also effective as a perforation sealer. ACP or a TTCP+DCPA mixture has been used as the mineral source in remineralizing dental restorative materials.

In addition to calcium phosphates, a number of calcium-containing compounds also have significant dental applications. Calcium fluoride, $CaF_2$, which is the major product of most topically applied F (F dentifrices, F rinses, professionally applied F gel, etc.), is the source of ambient F in the mouth that is primarily responsible for the cariostatic effects of F. The greater the amount of $CaF_2$ that adheres to the oral tissue surfaces after a F application, the greater is the oral F retention and therefore the F cariostatic effects. Calcium-silicate compounds, tricalcium silicate and dicalcium silicate, are the major components of mineral trioxide aggregates (MTA), a material that finds wide uses in endodontic procedures, such as root end and perforation fills and for apical closure in the apexification procedure. Calcium silicate hydrates (CSH), $xCa(OH)_2 \cdot ySiO_2zH_2O$, of varying Ca/Si/$H_2O$ ratios are among the products formed in MTA.

Defined broadly, the term "nanostructured" is used to describe materials characterized by structural features of less than 100 nm in average size (WTEX Panel Report on Nanostructure Nanodevices, 1999). Clusters of small numbers of atoms or molecules in nanostructured materials often have properties (such as strength, electrical resistivity and conductivity, and optical absorption) that are significantly different from the properties of the same matter at the bulk scale. In the case of calcium phosphates and other bioactive inorganic materials, there are a number of reasons to believe that the combination of small particle size and high reactivity can lead to performance advantages in a range of clinical applications. For example, as set forth in the description of the preferred embedment hereinafter, experimental results showed that nano sized HA, when incorporated into a TTCP+DCPA calcium phosphate cement caused a drastic reduction in setting time from 30 min to 10-12 min. It is anticipated that nano particles of other calcium phosphate phases, which are ingredients of the various calcium phosphate cements in clinical use, will also significantly improve the setting and other handling properties, e.g., cohesiveness, injectability, etc., of the cements.

The apatite crystallites in human bone, enamel, dentin and cementum are all extremely small in size and can be considered as nanostructured materials. Because HA is the prototype for bioapatites, which are in nano crystalline forms, extensive efforts have been made to produce synthetic nano HA materials. Methods that have been used for preparing nano HA material include chemical precipitation, in some cases followed by spray drying or hydrothermal treatment, sol-gel approach, microemulsion techniques, precipitation from complex solution followed by microwave heating, wet chemical methods incorporating a freeze drying step, mechanochemical synthesis, and eletrodeposition. Additional studies reported synthesis of composites of nano HA and bioactive organic components including HA-collagen, HA-chondroitin sulfate or HA-chitosan using direct precipitation method, nano HA-polyamide using HA slurry and solution method, and Ca-deficient nano HA-high molecular weight poly (D,L-lactide) through a solvent-cast technique.

Preparation of microcrystalline and nanocrystalline HA have also been disclosed in the patent literature. U.S. Pat. No. 5,034,352 discloses that Spray drying is the preferred technique for converting the gelatinous precipitate of hydroxyapatite into the fine dry articles suitable for use in the agglomeration process. U.S. Pat. No. 4,897,250 discloses that calcium phosphate, including hydroxyapatite, precipitated by the reaction can be withdrawn in a powder form by any conventional techniques such as filtration, centrigual separation, and spray drying. U.S. Pat. No. 6,033,780 discloses a manufacturing method of a spherical apatite by means of a slurry comprising hydroxyapatite as its main component which is dried and powdered to prepare aggregates of primary apatite particles, preferably, spray dried to form spherical particles. U.S. Pat. No. 6,558,512 discloses that one method for preparing dense, rounded or substantially spherical ceramic particles such as calcium hydroxyapatite is by spray drying a slurry of about 20 to 40 weight % submicron particle size calcium hydroxyapatite. U.S. Pat. No. 6,592,989 provides a method of synthesizing hydroxyapatite comprising the steps of preparing a mixed material slurry by dispersing calcium hydroxide powder into a phosphoric acid solution and conducting a mechanochemical milling treatment. U.S. Pat. No. 5,585,318 provides methods for producing nonporous controlled morphology hydroxyapatite granules of less than 8 µm by a spray-drying process. Solid or hollow spheres or doughnut shapes can be formed by controlling the volume fraction and viscosity of the slurry as well as the spray-drying conditions. Finally, U.S. Pat. No. 6,013,591 discloses a method for preparing nanocrystalline HA that involves precipitating a particulate apatite from solution having a crystallite size of less than 250 nm and a BET surface area of at least 40 m$^2$/g. In all of the prior art methods cited above, HA was precipitated from a solution. The slurry or emulsion containing the precipitated HA was spray-dried to produce fine particles.

In the above methods described in the scientific or patent literature, the nano HA materials are formed in a solution environment, and in most cases, the product is washed with water or other solvents to remove impurity or undesired components. Exposure of the nano particles to additional solution environments is likely to result in significant interactions between the particle surfaces and the solvent, leading to modifications of the surface properties and a reduction in the high reactivity innate to the nano particles. Thus, there has persisted the need to identify methods and apparatus for the manufacture of high purity, amorphous or nearly amorphous nano particles, especially those comprised of Ca and P.

SUMMARY OF THE INVENTION

Briefly, the present invention comprises methods for preparing nano particles, such as HA particles, by spray drying of a solution discharged through a nozzle in such a way that the nano particles form via in situ precipitation resulting from generally controlled evaporation of the solution in a chamber. The product formed is essentially free of undesired components or impurities such that the particles do not need to be washed. Thus, the particles need not be exposed to any solution environment and therefore will retain their original, highly reactive surfaces. By adjusting the composition of the solution, e.g., the Ca/P ratio, Na and carbonate concentrations, etc., nano HA particles of a range of Ca deficiency and substitution (Na for Ca and carbonate for phosphate) can be prepared. The spray drying methods and apparatus described hereinafter can be used to prepare not only nano HA, but also nano forms of MCPM, DCPD and/or DCPA, and OCP by appropriately formulating the solution composition which is to be sprayed to form droplets from which the liquid is evaporated.

Many compounds of biomedical interest, such as fluorapatite (FA), have very low solubilities so that a saturated solution would contain little amount of dissolved material. Other compounds, such a calcium fluoride, calcium silicate, etc., have low solubilities that do not increase significantly with increasing acid strength. As a result, the one-solution spray drying method as described hereinafter may not be as commercially useful as desired for preparing nano particles of these compounds. However, availability and use of two-liquid nozzles makes it possible to prepare nano particles of these insoluble salts because the cationic and anionic components of the salt are initially present in two separate solutions each one being dispersed from a distinct, but adjacent nozzle to enable ionic combination upon atomization in a chamber.

Thus, the invention is generically described as methods comprising preparation of nano structured materials using a spray drying technique employing a one-liquid nozzle or multiple liquid nozzles. An important feature of the inventive spray drying process comprises evaporation of the liquid from which the nano particles are derived thereby leading to in situ precipitation of HA (or another compound of interest) that is essentially free of undesired components or impurities. In this way the nano particles formed do not need to be washed and therefore not be exposed to any solution environment that could modify the particle surfaces. This process requires that the solution being sprayed contain only calcium and phosphate ions (or constituent ions of the salt to be prepared) and an acid component in water solution, if needed, to solubilize the calcium phosphate compound. The acid must preferably be sufficiently volatile so that it can be readily evaporated in the spray drying process. To achieve this, the volatile acid must preferably also be a weak acid such that no significant amounts of the acid anions, which are not volatile remain present by the end of the evaporation process. Precipitation of HA, for example, resulted from evaporation of water in the spray drying process causing a decrease in solution pH to about 4.0. This, in turn, makes the weak acid become increasingly more undissociated and therefore readily evaporated. Carbonic and acetic acids are examples of good candidates for the purpose. In the specific example of HA particle formation, HA-saturated solutions can be prepared by dissolving HA in a dilute acetic acid (for example, 17.5 mmol/L) solution (acetic acid-HA solution) or carbonic acid (266 mmol/L) solution (carbonic acid-HA solution).

Other examples of the methods of the invention include formation of nano particles of other components. For example, compositions of solution to be spray dried for preparing nano particles of various calcium phosphate phases are set forth in Table 2. Because MCPM is highly soluble, the solution for the nano MCPM production can be prepared by dissolving an appropriate amount of MCPM or other sources of Ca (for example $CaCO_3$) and P (for example $H_3PO_4$) in a solution of the desired concentration (Table 2). For the preparation of nano particles of other calcium phosphates, a volatile weak acid is used to facilitate solubilization of the calcium phosphate ions. The examples in Table 2 show acetic and carbonic acid as the volatile weak acids but other acids of similar properties could also be used. With the exception of MCPM, the amount of a calcium phosphate that can be dissolved is strongly affected by the concentration of the volatile acid. Table 2 shows examples of the solubility of various salts at two concentrations of carbonic acid or acetic acid. In general, a minimum amount of the volatile weak acid, necessary to keep the calcium and phosphate ions in the solution, is used to facilitate the removal of the acid in the spray drying process.

TABLE 2

Compositions of Spray Drying Solutions for Use in the Single-Liquid Nozzle Process

| For MCPM preparation [Ca]/[P] = 0.5 | | | |
| --- | --- | --- | --- |
| Solvent | [Ca] mmol/L | [P] mmol/L | pH |
| Water low | 0.1 | 0.2 | 4.9 |
| high | 2000 | 4000 | 4.0 |
| Acid | [Ca] mmol/L | [P] mmol/L | pH |
| DCPD/DCPA-saturated solution, [Ca]/[P] = 1.0 | | | |
| Carbonic Acid 1000 mol/L | 20.1 | 20.1 | 4.6 |
| Carbonic Acid 0 mmol/L | 1 | 1 | 8.4 |
| Acetic Acid 996 mmol/L | 109 | 109 | 3.6 |
| Acetic Acid 0 mmol/L | 0.1 | 0.1 | 8.4 |
| OCP-saturated solution, [Ca]/[P] = 1.33 | | | |
| Carbonic Acid 1018 mmol/L | 29.6 | 22.2 | 4.8 |
| Carbonic Acid 0.04 mmol/L | 0.1 | 0.075 | 8.8 |
| Acetic Acid 995 mmol/L | 221 | 166 | 4.0 |
| Acetic Acid 0.04 mmol/L | 0.1 | 0.075 | 8.8 |
| ACP- or TCP-saturated solution, [Ca]/[P] = 1.5 | | | |
| Carbonic Acid 1152 mmol/L | 147 | 98 | 5.4 |
| Carbonic Acid 0 mmol/L | 0.1 | 0.067 | 9.7 |
| Acetic Acid 985 mmol/L | 610 | 407 | 5.0 |
| Acetic Acid 0 mmol/L | 0.1 | 0.067 | 9.7 |

TABLE 2-continued

Compositions of Spray Drying Solutions for Use in the Single-Liquid Nozzle Process

| HA-saturated solution, [Ca]/[P] = 1.67 | | | |
| --- | --- | --- | --- |
| Carbonic Acid 1004 mmol/L | 14.2 | 8.54 | 4.6 |
| Carbonic Acid 0.164 mmol/L | 0.1 | 0.06 | 6.8 |
| Acetic Acid 998 mmol/L | 132 | 79 | 3.9 |
| Acetic Acid 0.122 mmol/L | 0.1 | 0.06 | 6.8 |
| Calcium hydroxide-saturated solution | | | |
| Solvent | [Ca] mmol/L | [P] mmol/L | pH |
| Water | 20.5 | 0.0 | 12.5 |
| Calcium sulfate-saturated solution | | | |
| Solvent | [Ca] mmol/L | [$SO_4$] mmol/L | pH |
| Water | 14.5 | 14.5 | 7.1 |
| For citric acid preparation | | | |
| Solvent | [Citric Acid] mmol/L | | pH |
| Water | 10 | | 2.6 |
| Water | 100 | | 2.1 |
| Water | 1000 | | 1.6 |

The spray formation and drying process in one embodiment thus comprises introduction of a solution of the compound or compounds described through a spray nozzle (nozzles) into a heated chamber where the spray particles are deliquified thereby resulting in high purity, solid, generally amorphous, nano particles collected in a precipitation. Two nozzles may be utilized for certain applications where the compounds would not otherwise adequately dissolve in a weak acid solution.

Thus, it is an object of the invention to provide methods for manufacture of nano particles of various compounds by a process which facilitates formation of high purity particles.

Another object of the invention is to provide methods for manufacture of nano particles that is efficient, and which avoids complex procedures.

A further object of the invention is to provide a method for manufacture of nano particles by spray drying techniques.

These and other objects, advantages and features of the invention will be set forth in the detailed description which follows.

BRIEF DESCRIPTION OF THE DRAWING

In the detailed description which follows, reference will be made to the drawing comprised of the following figures.

DESCRIPTION OF THE PREFERRED EMBODIMENT

Figure 1:
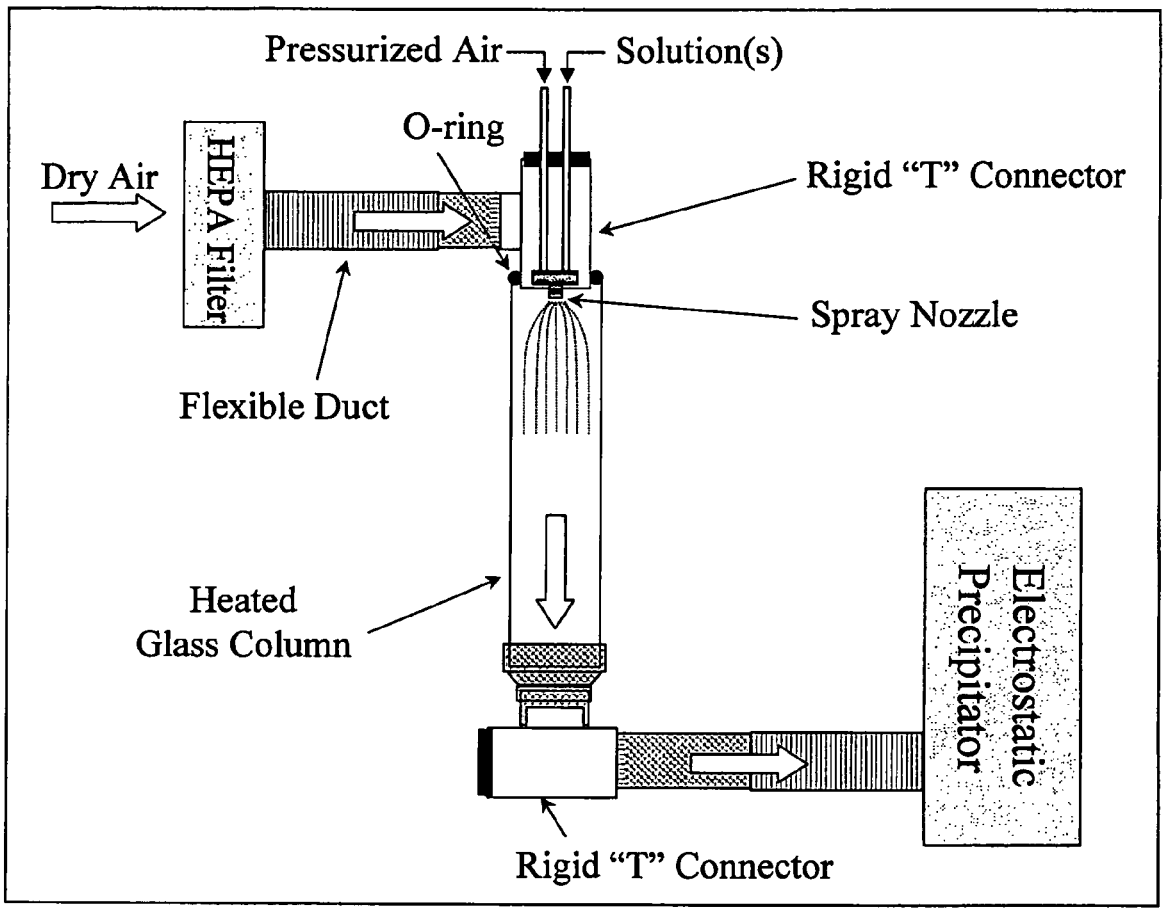
FIG. 1 is a schematic drawing which depicts an embodiment of a spray drying apparatus useful in the practice of the invention.

Referring to FIG. 1, there is depicted in a schematic view a device useful to form nano particles. The apparatus depicted in FIG. 1 consists of a spray nozzle 10 (SUC1120, PNR America LLC, Poughkeepsie, N.Y.) situated on the top of a glass column 12 (Model VM770-48, VM Glass Co., Vineland, N.J., 6" diameter), which is heated with electrical heating tapes (Model BIH 101100L, BH Thermal Co., Columbus, Ohio) and thermally insulated (fiberglass tape, Flextex, Montgomeryville, Pa.). Dry HEPA filtered air is supplied at the top 14 of the column, and an electrostatic precipitator 16 (MistBuster®, Air Quality Engineering, Inc., Minneapolis, Minn.) connected to the lower end of the column 12 pulls air from the column, creating a steady flow of air/mist through the column 12. The water and volatile weak acid in the solution are evaporated into the dry, heated air in the column and are expelled from the precipitator 16 into a hood. The fine particles suspended in the flow are trapped in the precipitator 16 and collected at the end of the process.

The nozzle utilized in the apparatus is selected to provide spray droplets of minimum size. Thus, the nozzle preferably has a diameter of the nozzle outlet passage in the range of about 12 to 15 microns for the compounds tested. The temperature in the dehydration chamber is typically in the range of 100° C. to about 200° C. without dissociation or adverse impact upon the formed particles. On the other hand, materials such as DCPA and DCPD are dehydrated at a temperature adequately under 200° C. to avoid dissociation or other adverse effects upon the formed particles. Of course, the flow rate of the clean air into the system will affect temperature in the forming chamber. The air may or may not be preheated.

The size and shape of the evaporation chamber will also comprise a factor affecting air flow rates, temperature and evaporation. An arrangement which avoids spray condensing or collecting on the chamber walls is highly preferred. The pH of the acid solution is also preferably controlled for reasons noted previously and preferably is about 4.0 or less. Of course, as the liquid evaporates to leave the powder particles, the effective pH increases. A weak acid is desired to preclude inclusion of acid based artifacts in the formed particles.

Characterization of the Nano Particles

XRD (Rigaku DMAX 2200, Rigaku Denki Co. Ltd. The Woodlands, Tex.) was used to determine the crystalline phases present in the formed nano particle product. Scans were performed between $10° < 2\theta < 50°$. The estimated standard uncertainty of the $2\theta$ measurement is 0.01° and the mass fraction of a crystalline phase to be detected by XRD is about 3%. It was anticipated that the product will contain primarily amorphous materials and the location and the intensity of the broad peak were noted.

A ThermoNicolet NEXUS 670 FT-1R spectrometer (Thermo Nicolet, Madison, Wis.) was used to record the infrared spectra of the nano powders. The formed nano particle powders were mixed with IIR quality KBr at a mass ratio of=1:400 and finely ground in a mortar and pestle. The mixture was then pressed into a pellet in a 13 mm diameter evacuated die. The sample KBr pellet to cancel the impurity bands. The absorbance spectra were acquired over the range of 400 $cm^{-1}$-4000 $cm^{-1}$ using a DTGS detector and KBr beam splitter, with a resolution of 2 $cm^{-1}$. Each spectrum was scanned 32 times to increase the signal-to-noise ratio. The estimated standard uncertainty of wavelength was ±4 $cm^{-1}$.

Multipoint Brunauer-Emmett-Teller (BET) surface area analyses were done (Gemini 2375 Surface Area Analyzer, Micromeritics, Norcross, Ga.) with ultra high purity nitrogen as the adsorbate gas and liquid nitrogen as the cryogen. The pressure sequence was (0.05, 0.10, 0.15, 0.20, 0.25) P/Po and the evacuation time was three minutes. The analysis mode was equilibration with the equilibration time of 5 s. The samples were dried in air overnight at 110° C. (Micromeritics Flow Prep station) before the measurement. Analyses were conducted on replicate samples to established standard deviation. In this and other measurements in the present study, the standard deviation was taken as the standard uncertainty.

A TA Q500 thermo gravimetric analyzer (TA Instruments—Waters LLC, New Castle, Del.) was used to determine the weight loss of the nano powder sample with the increase of temperature. The temperature range was from 25° C. to 950° C., and the heating rate was 10° C./min. Estimated standard uncertainty of temperature calibration was ±5° C.

Samples of the nano materials were analyzed for calcium (Ca) and phosphate (P) by spectrophotometric methods and carbon (C) by combusting the sample at 1000° C. in a constant oxygen flow and detecting the carbon dioxide by infrared absorption using a LECO CHN 000 Analyzer (St. Joseph, Mich.) [35,36]. This information was used in conjunction with FTIR data to estimate the chemical composition of the nano samples.

Transmission electron microscopy (TEM) was used in characterizing the particles. For this purpose, particles were deposited onto Cu grids, which support a "holey" carbon film. The particles were deposited onto the support grids by deposition from a dilute suspension in acetone or ethanol. The particle shapes and sizes were characterized by diffraction (amplitude) contrast and, for crystalline materials, by high resolution electron microscope (JEOL, Peabody, Mass.), equipped with a Gatan Image Filter (with parallel EELS) and a light element EDS system.

The transient nature of the dissolution behavior of HA was taken into consideration when conducting the solubility measurements as follows. The solubility experiments were conducted by dissolving the nano HA sample in solutions pre-saturated with crystalline HA at pH (5.0, 5.5, and 6.0). Based on calculations using a commercially available software "Chemist" (MicroMath, Salt Lake City, Utah), the solutions were prepared by equilibrating crystalline HA in 8.1 mmol/L, 2.7 mmol/L, and 0.92 mmol/L phosphoric acid solutions, that also contained 150 mmol/L KNO, as an electrolyte background, until saturation followed by filtration. In each solubility measurement conducted at (21±1) ° C., a pre-calibrated combination pH electrode [60110B, Extech Instruments Co., Waltham, Mass.] and a Ca-ion specific electrode [Orion 97-20 Ion Plus, Thermo Electron Co., Woburn, Mass.] were placed in 100 mL of a HA-saturated solution under constant stirring (52.4 rad/s or 500 rpm), and stable electrode readings were recorded ever 10 s, 5 mL of the equilibrating slurry was removed at (1, 2, 3, 4, 5 and 10) min and immediately filtered for analysis of [Ca] and [P] concentrations using spectrophotometric methods [34]. The pH, [Ca], and [P] values were used to calculate solution ion activity products (IAP) with respect to HA [Eq. (1)] and other calcium phosphate phases using the software "Chemist"

$$IAP(HA)=(Ca^{2+})^{10}(PO_4)^6(OH)^2 \quad (1)$$

where quantities in ( ) on the right hand side of equation denote ion activities. Solubility measurements were conducted on replicate samples to established standard deviation.

Properties of Nano HA Prepared from an Acetic Acid-HA Solution.

Figure 2:
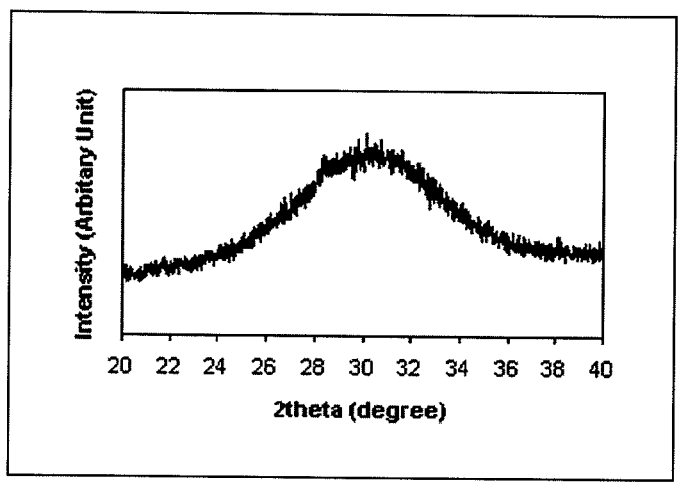
FIG. 2 is an x-ray diffraction pattern for HA nano particles prepared with acetic acid in accord with the invention.
Figure 3:
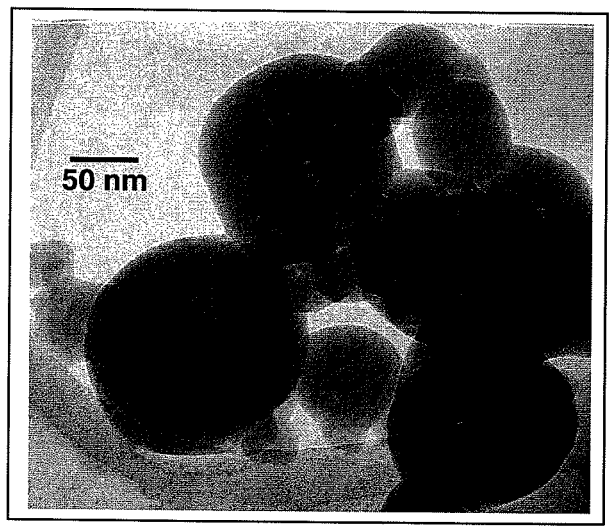
FIG. 3 is transmission electron microscope image of the HA nano particles prepared with acetic acid in accord with the method of the invention.
Figure 4:
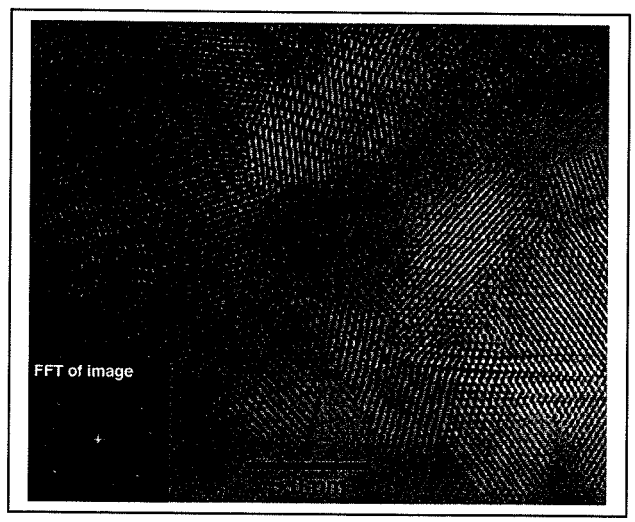
FIG. 4 is a high resolution transmission electron microscope image of HA nano particles prepared with acetic acid in accord with the method of the invention.
Figure 5:
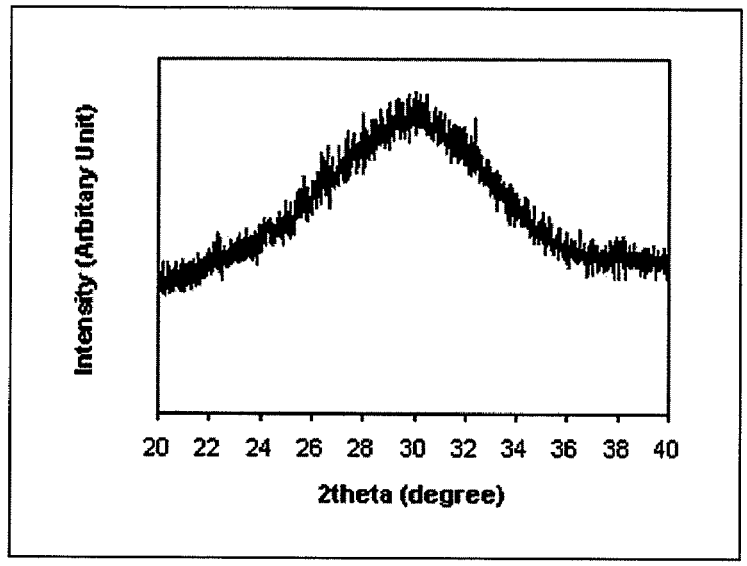
FIG. 5 is an x-ray diffraction patterns for HA nano particles prepared with carbonic acid in accord with the method of the invention.

Once brushed off the precipitator plates, the nano HA had the form of a white fine powder. Powder X-ray diffraction (XRD) patterns showed that the material was amorphous (FIG. 2). Transmission electron microscopic (TEM) observations show clusters that contained spherical particles about 10 nm to 100 nm in diameter (FIG. 3). High resolution TEM performed on particles that had been suspended in ethanol for 2 days showed packed crystalline HA particles 5 nm to 10 nm in size (FIG. 4). BET measurement results showed a surface area of (mean±standard deviation, n=2) (33.1±3.4) m$^2$/g, leading to a calculated (assuming spherical particles) mean particle size of 58 nm.

Fourier transformed infrared (FTIR) analyses of the samples showed a pattern indicative of HA with the presence of some acid phosphate (874 cm$^{-1}$, 1356 cm$^{-1}$, 1389 cm$^{-1}$), absorbed water, and acetate (670 cm$^{-1}$, 1417 cm$^{-1}$, 1462 cm$^{-1}$, 1568 cm$^{-1}$).

Elemental analysis showed that the materials had a carbon content of 5.79% mass fraction (5.79%) from acetate residue. Because calcium acetate is quite soluble and this may mask the true solubility of the nano HA, solubility measurements were not performed on this material.

The nano HA particles were used as seeds to determine whether the setting time of a calcium phosphate cement (CPC) could be reduced. Cement hardening or setting time was measured with a Gilmore needle apparatus using a heavy Gilmore needle (453.5 g load, 1.06 mm diameter). The sample was considered set when the needle fails to leave a visible indentation when placed over the surface of the cement. Two CPC mixtures were prepared. The control CPC consisted of equimolar amounts of TTCP (72.9%) and DCPA (27.1%), and the experimental CPC was a mixture that consisted of 95% control CPC and 5% nano HA seeds. The setting times of the control and experimental CPCs were 30±1 min (n=2) and 12±1 min, respectively. These results showed that the nano HA produced dramatic effects on the TTPC+DCPA cement setting times. Because of the similarities in setting reaction mechanism, the nano particles of calcium phosphate materials are expected to produce similar effects on setting times of CPCs of different compositions.

Properties of Nano HA Prepared from a Carbonic Acid-HA Solution.

Figure 6:
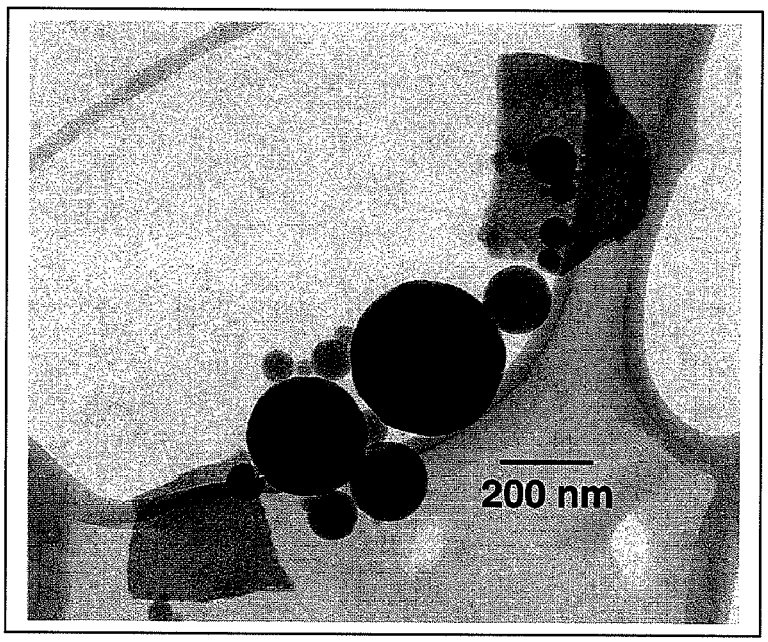
FIG. 6 is a transmission electron microscope image of HA nano particles prepared with carbonic acid in accord with the method of the invention.

The sample was a white powder. XRD patterns showed that the material was amorphous (FIG. 6). TEM observations showed clusters of porous spherical amorphous that arrange from 50 nm to about 1 μm in size (FIG. 4). BET analysis showed surface area of (7.17±0.19) m$^2$/g (n=2), leading to a calculated particle mean size of 266 nm. Because the material has the stoichiometry similar to that of HA but is amorphous under both XRD and TEM examinations, this material will be referred to as "amorphous HA" (AHA).

FTIR showed the pattern of amorphous calcium phosphate with the presence of some acid phosphate (870 cm$^{-1}$), adsorbed water (3407 cm$^{-1}$), molecular water (16435 cm$^{-1}$), and a large amount of trapped $CO_2$ (2342 cm$^{-1}$) as well as some carbonate incorporation in the structure (870 cm$^{-1}$, 1422 cm$^{-1}$, and 1499 cm$^{-1}$). Elemental carbon analysis showed the material also contained 9.1 percent mass fraction (9.1%) of carbon.

Figure 7:
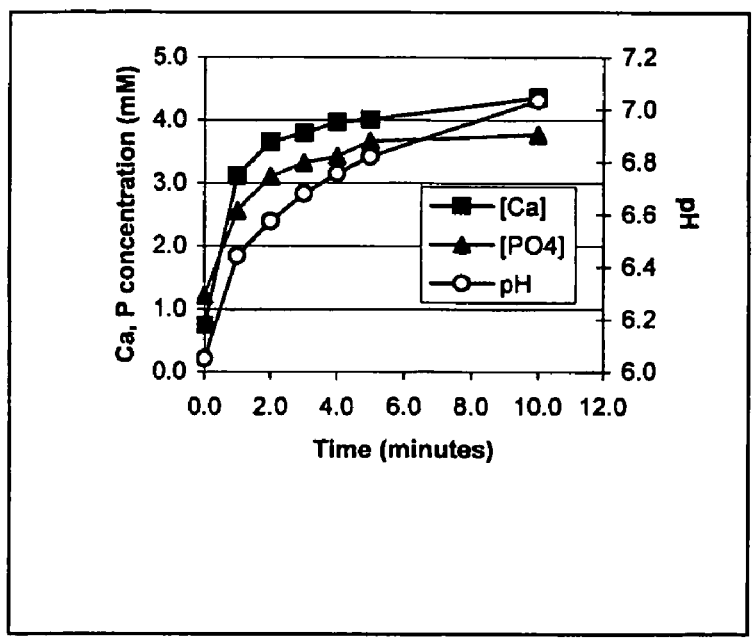
FIG. 7 is a graph depicting dissolution of HA in a pH 6 HA pre-saturated solution.

Solubility experiments were conducted by dissolving the nano HA in a solution presaturated with well crystalline HA. The HA-presaturated solution was prepared by equilibrating crystalline HA in a 0.92 mmol/L phosphoric acid solution that also contained 150 mmol/L KNO$_3$ as an electrolyte background until saturation followed by filtration. The solution had [CA] and [P] concentrations of 0.75 mmol/L and 1.22 namol/L, respectively, and a pH of 6.07. Dissolution experiment results showed that both the [Ca] and [P] concentrations as well as the pH increased rapidly with time (FIG. 7). This indicated that the nano-HA was much more soluble than the crystalline HA> The calculated pIAP(HA) value for the nano HA was (mean±standard deviation; n=2) 93.5±0.3, which is significantly less positive (indicating greater solubility) than the value of 117 for macro scale HA.

Thermal gravimetric analysis (TGA) showed that sample mass losses occurred at (60 to 120)° C., (210 to 380)° C., (440 to 580)° C. and (650 to 750)° C. Most of the trapped $CO_2$ was lost after being held for one hour in vacuum at 600° C. (FIG. 6c) and completely escaped after heating to 950° C. (FIG. 6d). The intensity of the carbonate bands in AHA (870 cm$^{-1}$, 1422 cm$^{-1}$ and 1499 cm$^{-1}$) decreased with increasing temperature (FIGS. 6a-c) and finally changed to type B (870 cm$^{-1}$, 1457 cm$^{-1}$, and 1552 cm$^{-1}$) and type A (870 cm$^{-1}$, 1457 cm$^{-1}$, and 1421 cm$^{-1}$) carbonate incorporation, substituting for phosphate and hydroxyl groups, respectively, as the AHA structure transformed to a carbonated HA after heating to 950° C. in vacuum.

The solubility results showed that in each dissolution experiment, the [Ca] and [P] concentrations as well as the pH increased rapidly with time. This indicated that the nano-HA was much more soluble than the crystalline HA. For dissolution experiments conducted with pH 5.0 and pH 5.5 HA-presaturated solutions, rapid increases in [Ca] and [P] were followed by gradual decreases in these concentrations starting at about 2 min., while the pH continued to increase. This observation suggested that a less soluble HA phase began to precipitate as the nano HA continued to dissolve. The calculated PiAP(HA)=–log [IAP(HA)] (see Eq. (1) for IAP definition) values were (mean ±standard deviation; n=2) 99.7±0.2, 97.2±0.4 and 93.5±0.3, respectively, for data obtained from dissolution experiments with HA-presaturated solutions having pH 5.0, 5.5 and 6.0. The smaller IAP values (more positive pIAP values), observed at the lower pHs probably was, in part, a result of the simultaneous dissolution-precipitation phenomenon.

More specifically, HA prepared from carbonic acid would likely be more soluble than crystalline HA, both because of its small particle size and $CO_2$ content. An IAP(HA) value as high as $3.3 \times 10^{-94}$ (pIAP=93.6), compared to $1 \times 10^{-117}$ for crystalline HA, was obtained from experiments in which the nano HA was dissolved in the pH 6 HA-presaturated solution. In this dissolution run, the [Ca] concentration increased from the initial value of (0.75±0.01) mmol/L in the crystalline HA-presaturated solution to a near a plateau value of (4.5±0.2) mmol/L at 10 min when the experiment ended. The [P] concentration similarly increased from the initial value of (1.2±0.1) mmol/L to a stable value of (3.5±0.2) mmol/L at 5 min. The pH of the solution continued to increase and reached 7.03±0.01 at 10 min. Dissolution of the same nano HA into the pH 5 HA-presaturated solution led to initial increases in [Ca] and [P] concentrations as in the pH 6 experiment. However, the initial increases were followed by continued decreases in these concentrations beginning at about 2 min to levels that were below the starting [Ca] and [P] concentrations. These results suggested that addition of nano HA to a pH 5 HA-saturated solution led to sustained precipitation of crystalline HA. Such a process might be useful for remineralizing dental carious lesions or for occluding open dentinal tubules as a treatment for dental hypersensitivity.

Both nano HA samples, prepared with acetic acid and carbonic acid, appeared amorphous in SRD, but the former HA was crystalline as revealed by high resolution TEM despite the extremely small particle sizes of 5 nm to 10 nm. It is noted that this sample for the high resolution TEM analysis was suspended in ethanol for 2 days and there is a possibility that a phase transformation may have occurred during this period. However, under similar sample handle conditions, the carbonic acid derived nano HA remained amorphous under TEM analysis.

Because the acetic acid- and carbonic acid-HA solutions had identical [CA] and [P] concentrations and the spray drying processing conditions were essentially the same, the differences in crystallinity of the nano HA samples prepared from the two solutions may be attributable to factors related to the nature of the acids.

Process Comparison

As described above, by using a minimal amount of a volatile weak acid to prepare the spray drying solutions, the process is capable of producing HA materials that contain little or no impurity components. In practice, a fair amount of acetate was found in the nano HA sample prepared with the acetic acid-HA saturated spray drying solution, and a large amount of trapped $CO_2$ was present in the nano HA prepared with the carbonic acid-HA saturated solution. The amount of residual acid components in the spray dried product could be reduced by using a more dilute solution, i.e., with lower [Ca] and [P] concentrations, because a smaller amount of acid would be required to prepare the solution. A complication with HA preparation in general is that HA has a high "affinity" for carbonate. Carbonate is readily incorporated into the HA structure in conventional HA preparation processes unless measures are taken to exclude $CO_2$ from the system. Because HA is the most alkaline salt among all calcium phosphates that can be prepared in an aqueous system, a larger amount of acid is needed to prepare HA saturated solutions compared to saturated solutions of the other calcium phosphates. Consequently, the residual acid problem is most pronounced in the HA preparation. Preliminary data indicates that no residual acid was present in dicalcium phosphate dihydrate nano particles prepared by this process. These observations indicate that the spray drying technique should be useful for preparing nano particles of a range of calcium phosphate phases with minimum impurities.

Multiple Nozzle Techniques

Many compounds of significant biomedical of industrial interests have low solubilities under all pH conditions. As a result, the spray drying technique described above using a one liquid nozzle is not useful because it is impossible to prepare a solution that contains a significant amount of dissolved mass of the salt. Availability of a two liquid nozzle makes it possible to prepared nano particles of these compounds because the cationic and anionic components of the salt are present in separate solutions that are combined only at the time of spraying. Nozzles that can simultaneously spray than two liquids can be constructed following the same principle as that for the single liquid nozzle. Thus, the spray drying process described here can be used for multi-liquid systems when needed to keep incompatible components in separate liquids, which are mixed at the time of atomization and spray drying.

Materials

The compositions of the solutions to be spray dried for preparing nano particles of several compounds are given in Table 3. It is noted that in some cases, such as in the preparation of F-substituted apatites, solution 1 will contain (Ca(OH)$_2$ and solution 2 will contain $H_3PO_4$ and HF. Upon mixing and spray drying the two solutions, only water needs to be evaporated to produce FA or a F-substituted apatite. In other cases, an acid (or a base) is needed to solubilize the cationic (or anionic) component, and the acid will also need to be evaporated during the spray drying process. An example for this is the preparation of calcium silicate hydrate (CSH). Because $SiO_2$ is insoluble in acid but is slightly soluble in concentrated alkaline, amorphous $SiO_2$ is dissolved in a $NH_4OH$ solution, and $NH_3$ will be evaporated together with water during the spray drying process.

TABLE 3

Composition of Spray Drying Solutions for Use in the Two-Liquid Nozzle Process

For calcium phosphate preparation

Solution 1  Ca(OH)$_2$    1 to 15 mmol/L; pH from 11.3 to 12.2
Solution 2  $H_3PO_4$     [P] = (0.5 to 2) × [Ca]; pH from 4.4 to 4.9
Example of reaction: $5Ca(OH)_2 + 3H_3PO_4 \rightarrow Ca_5(PO_4)_3OH + 9H_2O \uparrow$ For FA preparation Solution 1  mmol/L        1 to 15 mmol/L; pH from 11.3 to 12.2
            Ca(OH)$_2$
Solution 2  $H_3PO_4$ + HF  [P] = ⅗ × [Ca]; [F] = (1/500 to ⅕) × [Ca]; pH from 3.2 to 2.2
Example of reaction: $5Ca(OH)_2 + 3H_3PO_4 + HF \rightarrow Ca_5(PO_4)_3F + 10H_2O \uparrow$ For CaF$_2$ preparation Solution 1  Ca(OH)$_2$    1 to 15 mmol/L; pH from 11.3 to 12.2
Solution 2  NH$_4$F        [F] = 2 × [Ca]; pH from 7.3 to 7.8
Example of reaction: $Ca(OH)_2 + NH_4F \rightarrow CaF_2 + NH_3 \uparrow + H_2O \uparrow$ For Calcium silicate hydrate (CSH) preparation Solution 1  Ca(OH)$_2$    1 or 15 mmol/L; pH from 11.3 to 12.2
Solution 2  SiO$_2$ in 1 N  [Si] = (0.1 to 1) × [Ca]; pH from 13.8 to 13.8
            NH$_4$OH Example of reaction: $xCa(OH)_2 + ySiO_2 + zH_2O \rightarrow xCa(OH)_2 \cdot ySiO_2 \cdot zH_2O$ Two Nozzle Methods The spray drying apparatus (FIG. 1) described for one-liquid spray drying process is used except that a 2-liquid nozzle (ViscoMist™ Air Atomizing Spray Nozzle, Lechler Inc., St. Charles, Ill.) is employed. This nozzle will simultaneously atomize two liquids that are mixed at the moment of atomization.

Results of Example of Two Nozzle Spray Method

Figure 8:
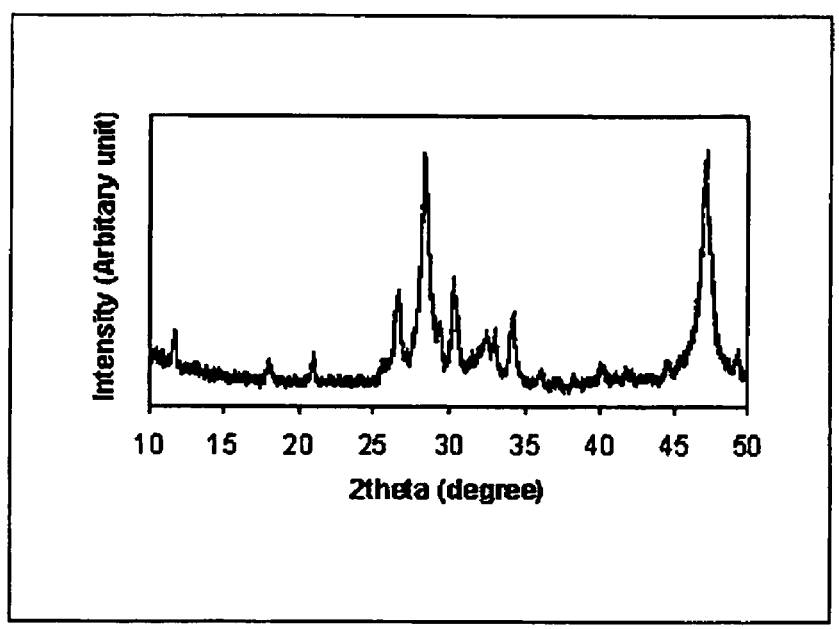
FIG. 8 is an x-ray diffraction pattern of nano particles of $CF_2$ prepared in accord with an alternative method of the invention utilizing two spray nozzles.

Nano particles of $CaF_2$ was prepared by spray drying a 10 mmol/L Ca(OH)$_2$ solution and a 20 mmol/L ammonium fluoride (NH$_4$F) solution that were combined at the time of atomization. XRD analysis (FIG. 8) showed crystalline $CaF_2$ despite that the particles are submicron in size.

Figure 9:
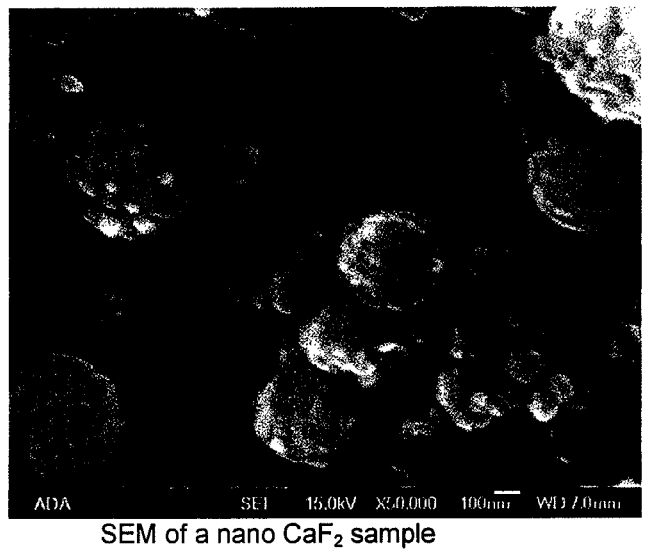
FIG. 9 is a scanning electron microscope image of a nano $CaF_2$ sample.
Figure 10:
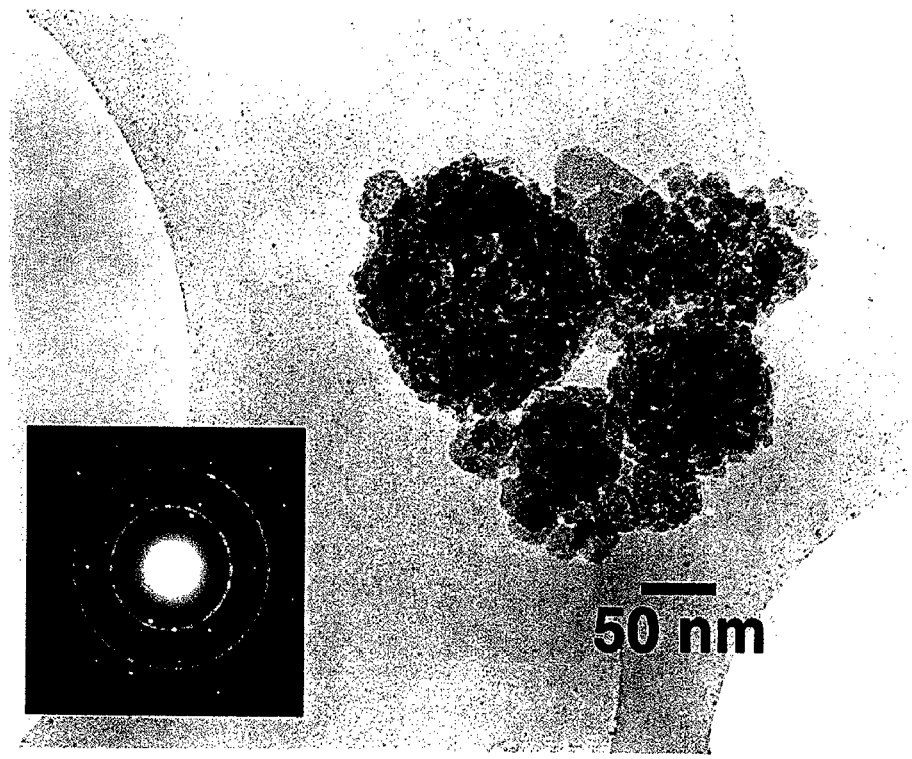
FIG. 10 is a transmission electron microscope image of a nano $CaF_2$ sample.

Preparation and Properties of Nano Calcium Fluoride, CaF$_2$, Particles Using a Spray Drying Method Employing a 2-Liquid Nozzle A 2 mmol/L Ca(OH)$_2$ solution and a 4 mmol/L ammonium fluoride (NH$_4$F) solution were atomized and spray dried. Mixing of the Ca(OH)$_2$ and NH$_4$F solutions led to formation of CaF$_2$ and NH$_4$OH; the latter was removed as NH$_3$ gas in the drying process. The CaF$_2$ nano particles were collected by the electrostatic precipitator as described before. XRD analysis showed crystalline CaF$_2$ with trace amount of DCPD also present due to contaminations from the precipitator plates. SEM examinations indicated that particles ranged from <50 nm to about 500 nm in size, see FIG. 9 and FIG. 10. The larger particles exhibited numerous spherical protuberances on the surfaces, suggesting that they were formed during the spray drying process through fusion of the much smaller particles. This suggests that well dispersed small particles could be produced by using a much lower spray rate. BET measurements showed that this sample has a surface area of 35.5 m$^2$/g, corresponding to a particle size of 53 nm. Transmission electron microscopic examinations confirmed that the nano calcium fluoride contained clusters comprised of still smaller particles of 10 to 15 nm in size (FIG. 3). This indicates that better dispersed individual particles can be produced by using more dilute solutions and with a lower spraying rate. Chemical reactivity of the nano CaF$_2$ was evaluated by stirring (300 rpm) 33 mg of the nano CaF$_2$ in a 30 mL of a solution pre-saturated with crystalline CaF$_2$. Specific ion electrodes for Ca and F and a combination pH electrode monitored the changes in [Ca] and [F] concentrations and pH. The results showed that both the [Ca] and [F] concentrations increased nearly by a factor of 2 and the solubility product (Ksp of the nano CaF$_2$) was $(2.3\pm0.2)\times10^{-10}$ which is about 6 times greater than the Ksp of value of $3.9\times10^{-11}$ for crystalline CaF$_2$. These results indicated that the nano CaF$_2$ is significantly more reactive than macro CaF$_2$.

In another test, mixtures containing a macro (median size 1.6 μm) DCPD and either the nano CaF$_2$ or a macro CaF$_2$ were mixed with water (1g/1 mL) and the pastes were left in 100% humidity at 37° C. for 24 h. XRD patterns showed that there was no reduction in the amount of the macro CaF$_2$ whereas the nano CaF$_2$ was partially consumed by reacting with the DCPD forming a larger amount of apatitic product. DCPD was nearly completely consumed in either mixture. These results showed the nano CaF$_2$ was more reactive than the macro CaF$_2$. It also indicated that the nano CaF$_2$ was not as reactive as the macro DCPD, suggesting that it would be necessary to use even smaller nano CaF$_2$ particles in order to have the CaF$_2$ dissolve in time for the reaction.

A Filter Paper Model for Evaluation of Fluoride Deposition by a Nano CaF$_2$ Prepared by the Spray Drying Method The ability of the nano CaF$_2$ to be attached to tooth and other oral substrate surfaces was evaluated in vitro using a filter disc model. Five filter discs (Millipore, Bedford, Mass.) with a pore size of 0.2 μm and pore volume of 75% were placed in 20 mL of a nano CaF$_2$ water suspension or a NaF solution (250 ppm total F in either case). After 1 min of exposure, the filters were rinsed twice in 50 mL of a solution saturated with respect to CaF$_2$ to remove particles that were not firmly attached on/in the disc or remove unreacted F ions. Firmly fixed CaF$_2$ particles would not be lost to the washing solution by dissolution because the solution was presaturated with respect to CaF$_2$. The F content in each disc was them determined by a F ion selective electrode method. F deposition on samples immersed in the nano CaF$_2$ suspension was 2.3±0.3 μg/cm$^2$ of surface area (n=5) which was significantly 9p<0.001) greater than that (0.31±0.06 μg/cm$^2$) produced by the NaF solution. These results showed that the nano CaF$_2$ particles were able to penetrate into the pores and fixed onto the substrate. Previous studies have shown a good correlation between the F deposition on the filter disc substrate and that on sound enamel. Thus, the results suggest that the nano CaF$_2$ suspension should be more effective than the currently used NaF solution for increasing oral F level.

Use of Nano Calcium Fluoride for Oral Fluoride Rinse and Dentifrice Applications The following are examples of rinse and dentifrice formulations that include nano calcium fluoride:

EXAMPLE 1

The following two F rinses, both containing 250 ppm of F, were evaluated for their efficacy in depositing F in an in vitro model.

| Rinse Composition | | F deposition (μg/cm$^2$) |
|---|---|---|
| 1 | 0.055 g NaF dissolved in 100 g water | 0.31 ± 0.06 (n = 5) |
| 2 | 0.051 g nano CaF$_2$ suspended in 100 g water | 2.3 ± 0.30 (n = 5) |

The F deposition by the inventive rinse using nano calcium fluoride as the fluoride source produced more than 7 times higher F deposition than the conventional sodium fluoride rinse. The inventive rinse was about equally effective than a novel two-component rinse (U.S. Pat. No. 5,891,448) which produce F deposition of 2.62±0.16 μg/cm$^2$. However, the inventive rinse has the advantage of being a single component rather than a two-component product.

EXAMPLE 2

The following is an example of the composition of a 250 ppm F mouth rinse using the inventive nano calcium fluoride:

| | |
|---|---|
| ethyl alcohol (95%) | 20 grams |
| glycerol | 8.0 |
| sorbitol (70% solution) | 10 |
| sodium lauryl sulfate | 0.5 |
| sodium lauryl sarcosinate | 0.5 |
| sodium saccharin | 0.1 |
| nano calcium fluoride | 0.103 |
| water, coloring, flavoring | balance |
| Total | 100 grams |

EXAMPLE 3

The following is an example of the composition of a 1000 ppm F dentifrice using the inventive nano calcium fluoride:

| | |
|---|---|
| calcium glycerophosphate | 4.2 grams |
| nano calcium fluoride | 0.411 |
| sorbitol (70% solution) | 15 |
| silica | 35 |
| glycerol | 15 |
| carboxymethyl cellulose | 1 |
| sodium n-lauryl sarcosinate | 1 |
| water, coloring, flavoring | balance |
| Total | 100 grams |

Effect of a Nano CaF$_2$ Oral Rinse on Salivary F Levels

This study evaluated the effects of an oral rinse with the nano CaF$_2$ water suspension used in the above experiment on salivary F levels. Five subjects (1 hour without food or drink) rinsed for 1 min 20 mL of a nano $CaF_2$ water suspension (10.3 mg $CaF_2$ in 20 mL, 250 ppm total F) or a control F rinse (250 ppm F from NaF) and expectorated the rinse. Saliva sample was collected 1 hour post rinse and analyzed for F significantly (p=0.004, a log-transformation was performed to obtain normally distributed samples) higher F level (158 µg/mL) compared to that produced by the control rinse (36 µg/mL). This observation suggests that the nano $CaF_2$ rinse should be significantly more effective than the currently used F regimens. Because the nano $CaF_2$ material used in this study had a wide range of particle sizes (from <50 nm to about 500 nm), it is likely that an even more effective rinse could be developed by using nano $CaF_2$ with an optimal particle size distribution.

Preparation of Nano Calcium Phosphate-Polymer Composites Using the 2-Liquid Nozzle Spray Drying Technique The first liquid contains a calcium phosphate solution given in Table 2 for preparing a calcium phosphate. The second liquid contains a polymer dissolved in an aqueous solution or in a non-aqueous solvent that is miscible with water. Nano particles of calcium phosphate-polymer composites with highly homogeneous calcium phosphate/polymer intermixture are formed in the spray drying process. Examples of calcium phosphates are HA, calcium-deficient HA, carbonated HA, Fluoride containing HA, amorphous calcium phosphate, tricalcium phosphate, dicalcium phosphate dihydrate, dicalcium phosphate anhydrous, monocalcium phosphate monohydrate, and monocalcium phosphate anhydrous. Examples of polymers to be used include chitosan, collagen, chrondroitin sulfate, polyamide, poly (D,L-lactide), alginate, and pectinate.

Summary of Factors Affecting Methods of Particle Formation

The methods disclosed in the invention are useful for preparing nano particles of any compound that can be formed by precipitation from an aqueous solution. The temperature under which the spray during process occurs is controllable by controlling the inlet air temperature and the temperature of the column (FIG. 1). Air temperature in the range from −185° C. to 800° C. can be obtained using commercially available equipment. Similarly, a wide range of the column temperatures can be readily obtained using commercially available equipment. The wide range of temperatures facilitates preparation of materials that would form most readily at different temperatures.

The inventive method is suitable for preparing particles from 1 nm to 100 µm in size. The particle size can be controlled by (1) the concentration of the compound in the solution to be spray dried, (2) size of the atomized droplets, i.e., nozzle design. Droplet size is preferably less than the final particle size and thus less than about 100 µm. Chamber design is also a factor. The chamber is generally designed to minimize collection of condensate i.e., liquid from on the chamber walls.

The nature and composition of the compound that will be formed will depend on the solution composition. In many cases, the solution pH is the most important factor because, for calcium phosphates and other compounds that are salts of weak acids, it is the pH that determines the solid phase that would precipitate as the water evaporates from the solution.

The purity of the compound prepared, i.e., being free from undesired components, is dependent on the ability of spray drying process to remove the acid or base used to dissolve the compound in the spray drying solution. The acid/base must be a weak acid/base so that a substantial portion of the acid/base is in undissociated form, and the acid/base is almost totally undissociated as the last portion of the liquid is evaporated. The undissociated acid/base must also be sufficiently volatile to facilitate evaporation of the acid/base.

The nano particles prepared by the methods disclosed in the invention are useful in any application in which the compound is currently useful but a performance advantage can be gained by having a higher reactivity and/or smaller particle size. Examples of this include (1) accelerated hardening of calcium phosphate cements when one or more calcium phosphate nano particles are included in the ingredients, (2) accelerated hardening of mineral trioxide aggregate (MTA) when one or more calcium silicate nano particles are included in the ingredients, (3) desensitization of teeth by effective obturation of exposed dentin tubule opening with calcium phosphate nano particles, (4) deposition of fluoride in/on oral tissue by application of agents that contain calcium fluoride or other fluoride nano particles. (5) as a source of calcium, phosphate, or fluoride in remineralizing dentifrices, gels, rinses, chewing gums, and candies; and (6) as a source of calcium, phosphate, or fluoride for formulating scaffolds for bone defects repair.

Thus, examples of compounds of biomedical interests that can be prepared by the spray drying method:
(1) The calcium phosphate and other compounds named in Tables 1, 2 and 3.
(2) Calcium containing compounds that may be used as a source of calcium for remineralization of teeth or for formulation of scaffolds for bone defects repair. Examples are calcium lactate, calcium gluconate, calcium glycerophosphate, calcium acetate, calcium fumarate, calcium citrate, calcium malate, calcium chloride, calcium hydroxide, calcium oxide, calcium carbonate.
(3) Phosphate containing compounds that may be used as a source of phosphate for remineralization of teeth or for formulation of scaffolds for bone defects repair. Examples are the monobasic, dibasic and tribasic phosphate salts of sodium, potassium, and ammonium.
(4) Fluoride containing compounds that may be used as a source of fluoride for remineralization of teeth or for formulation of scaffolds for bone defects repair. Examples are sodium fluoride, potassium fluoride, fluorophosphates fluosilicate, flurortitanate, and fluorostannate salts of ammonium, sodium, potassium and calcium.

While various techniques and apparatus have been described with particularity the invention is subject to variations and this is to be limited only by the following claims and equivalents thereof.

What is claimed is:

1. A method for manufacture of high purity, nanosized particles of a partially water soluble compound for in vivo use, said compound comprised of a first component and a second component, said components capable of precipitation in chemical combination as solid particles of said compound, said method comprising the steps of;
   (a) forming a first solely liquid solution of said first component of said compound and a weak acid liquid solvent of said first component;
   (b) forming a second solely liquid solution of said second component of said compound and a second liquid solvent of said second compartment, said first and second solutions each including ionic species in solution derived from the first and second compounds respectively;
   (c) directing said first and second solutions with a gas through a respective first and a second spray nozzle to generally simultaneously and separately atomize each of said first and second solutions into a spray;

(d) directing and combining said first and second atomized solutions into a common chamber at a temperature to evaporate the first and second liquid solvents and effect thereby chemical combination of ionic species derived from said first and second components to form said compound as dry nano particles; and (e) collecting said nano particles.

2. The method of claim 1 wherein said collecting step includes electrostatic precipitation of dried particles.

3. The method of claim 1 wherein said compound is selected from the group consisting of FA, $CaF_2$, CSH and CP; and said second solvent is selected from the group consisting of water, a weak acid, and a base.

4. The method of claim 3 wherein said weak acid solvent has a pH of about 4.0.

5. The process of claim 1 wherein in the step of atomizing at least one of said solutions comprises spraying through at least one of said nozzles having an orifice with an effective discharge opening of less than about 15 microns.

6. The process of claim 1 wherein the components comprise a first solution of $Ca(OH)_2$ and a second solution of $H_3PO_4$, each solution being separately discharged substantially simultaneously through a separate one of said spray nozzles into the same chamber to form $Ca_5(PO_4)_3OH$ particles.

7. The process of claim 1 wherein the components comprise a first solution of $Ca(OH)_2$ and a second solution of $H_3PO_4$ and HF, each solution being separately discharged into the chamber through a separate one of said spray nozzles substantially simultaneously to form $(Ca_5(PO_4)_3F)$ particles.

8. The process of claim 1 wherein the components comprise a first solution of $Ca(OH)_2$ and a second solution of $NH_4F$, each solution being separately discharged into the chamber through a separate one of said spray nozzles substantially simultaneously to form $CaF_2$ particles.

9. The process of claim 1 wherein the components comprise a first solution of $Ca(OH)_2$ and a second solution of $SiO_2$ in one normal $NH_4OH$, each one of said solutions being discharged substantially simultaneously into said chamber to form CSH particles.

10. The method of claim 1 including the further step of compounding said particles in a formulation selected from the group consisting of a dental rinse and a dentifrice.

11. The method of claim 10 including the step of compounding a dental rinse and employing the dental rinse in vivo as an oral rinse.

* * * * *

UNITED STATES PATENT AND TRADEMARK OFFICE
CERTIFICATE OF CORRECTION

PATENT NO. : 7,670,579 B2
APPLICATION NO. : 11/228139
DATED : March 2, 2010
INVENTOR(S) : Laurence C. Chow et al.

It is certified that error appears in the above-identified patent and that said Letters Patent is hereby corrected as shown below:

Column 1, line 57
    Please replace "Ca(H2PO4)2H2O" with -- Ca(H2PO4)2 H2O --

Column 1, line 64
    Please replace "CaHOP42H2O" with -- CaHPO4 H2O --

Column 8, line 58
    Please replace "KNO" with -- KNO3 --

Column 10, line 13
    Please replace "namol/L" with -- mmol/L --

Column 10, line 17
    Please replace "HA>" with -- HA. --

Column 11, line 10
    Please replace "SRD" with -- XRD --

Column 11, line 64
    Please replace "spray than" with -- spray more than --

Column 12, line 66
    Please replace "NH4F)" with -- NH4F --

Signed and Sealed this

Eleventh Day of May, 2010

David J. Kappos
*Director of the United States Patent and Trademark Office*